(12) United States Patent
Ruan et al.

(10) Patent No.: US 10,190,986 B2
(45) Date of Patent: Jan. 29, 2019

(54) SPATIALLY RESOLVED LIGAND-RECEPTOR BINDING ASSAYS

(75) Inventors: Qiaoqiao Ruan, Kildeer, IL (US); Sylvia C. Saldana, Hinsdale, IL (US); Joseph P. Skinner, Lake Villa, IL (US); Sergey Y. Tetin, Lindenhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 841 days.

(21) Appl. No.: 13/153,934

(22) Filed: Jun. 6, 2011

(65) Prior Publication Data
US 2012/0308997 A1    Dec. 6, 2012

(51) Int. Cl.
*G01N 21/00* (2006.01)
*G01N 21/64* (2006.01)

(52) U.S. Cl.
CPC ................. *G01N 21/6456* (2013.01)

(58) Field of Classification Search
None
See application file for complete search history.

(56) References Cited

U.S. PATENT DOCUMENTS

| 4,275,149 A | 6/1981 | Litman et al. | |
|---|---|---|---|
| 6,268,223 B1 * | 7/2001 | Cornell-Bell | G01N 33/6893 435/7.1 |
| 2003/0215791 A1 * | 11/2003 | Garini | B82Y 5/00 435/5 |
| 2003/0219764 A1 * | 11/2003 | Imoto | G06F 19/12 435/6.13 |

(Continued)

FOREIGN PATENT DOCUMENTS

| JP | H08334511 A | 12/1996 |
|---|---|---|
| JP | 2002537563 | 11/2002 |

(Continued)

OTHER PUBLICATIONS

Pitschke (1998) Nature Medicine 4: 832-834.*

(Continued)

*Primary Examiner* — Melanie Yu Brown
*Assistant Examiner* — Richard Moerschell
(74) *Attorney, Agent, or Firm* — Melissa E. Kolom; Casimir Jones, S.C.

(57) ABSTRACT

A method for analyzing the results of a ligand-receptor binding assay comprising the steps of:
(a) providing the results of a ligand-receptor binding assay; and
(b) qualifying the results of a ligand-receptor binding assay.

More particularly, the ligand-receptor binding assay involves the steps of combining appropriate reagents in which receptors attached to a solid support, a sample suspected of containing a ligand, and a conjugate comprising a label form a complex in which the label is present at a concentration that is directly proportional to the amount of ligand present in the sample. Alternatively, the ligand-receptor binding assay involves the steps of combining appropriate reagents to perform a ligand-receptor binding assay in which receptors attached to a solid support, a sample suspected of containing a ligand, and a conjugate comprising a label form a complex in which the label is present at a concentration that is inversely proportional to the amount of analyte present in the sample.

13 Claims, 18 Drawing Sheets

Antibody-Antigen-Labeled Antibody Sandwich

(56) References Cited

U.S. PATENT DOCUMENTS

| | | | |
|---|---|---|---|
| 2004/0241854 A1* | 12/2004 | Davidson et al. | 435/455 |
| 2005/0273011 A1 | 12/2005 | Hattery | |
| 2006/0121471 A1* | 6/2006 | Koh et al. | 435/6 |
| 2007/0166200 A1* | 7/2007 | Zhou | B01L 3/5025 422/400 |
| 2010/0069550 A1* | 3/2010 | Gao et al. | 524/401 |
| 2011/0007955 A1* | 1/2011 | Ho et al. | 382/128 |
| 2012/0013779 A1* | 1/2012 | Hattery | A61B 5/0059 348/302 |
| 2012/0225447 A1* | 9/2012 | Cho | G01N 33/582 435/29 |

FOREIGN PATENT DOCUMENTS

| | | |
|---|---|---|
| JP | 2004361158 | 12/2004 |
| JP | 2005508495 | 3/2005 |
| JP | 2011516863 | 5/2011 |
| WO | 2003/036290 | 5/2003 |
| WO | 2005064319 A1 | 7/2005 |
| WO | 2009/124179 | 10/2009 |

OTHER PUBLICATIONS

Camera Histograms: Tones & Contrast, [retrieved on May 13, 2011]. Retrieved from the Internet:<URL: http://www.cambridgeincolor.com/tutorials/histograms1.htm>.

Cyanine, From Wikipedia, the free encyclopedia, [retrieved on May 13, 2011]. Retrieved from the Internet:< URL: http://en.wikipedia.org/wiki/Cyanine>.

FITS, From Wikipedia, the free encyclopedia, [retrieved on May 11, 2011]. Retrieved from the Internet:< URL: http://en.wikipedia.org/wiki/FITS>.

Image file formats, From Wikipedia, the free encyclopedia, [retrieved on May 11, 2011]. Retrieved from the Internet:< URL: http://en.wikipedia.org/wiki/Image_file_formats>.

Jackson Immuno Research Expands Due to Increasing Demand for Its Products Worldwide, [retrieved on May 24, 2011]. Retrieved from the Internet:<URL: http://www.jacksonimmuno.com/technical/f-cy3-5.asp>.

Phycoerythrin, From Wikipedia, the free encyclopedia, [retrieved on May 13, 2011]. Retrieved from the Internet:< URL: http://en.wikipedia.org/wiki/Phycoerythrin>.

R-Phycoerythrin (PB31), Prozyme Inc.

Tetin S., "Quantitative Characterization of Ligand Binding" Winzor D.J., et al., eds., A John Wiley & Sons, Inc., 1995, Table of Contents.

Ubic R., MSE 421/521 Introduction to Electron Microscopy, pp. I(1)-I(11).

Eigen M., et al., "Sorting Single Molecules: Application to Diagnostics and Evolutionary Biotechnology," Proceedings of the National Academy of Sciences, 1994, vol. 91 (13), pp. 5740-5747.

International Search Report for Application No. PCT/US2012/040925, dated Aug. 24, 2012, 5 pages.

Rosales T., et al., "Quantitative Detection of the Ligand-dependent Interaction Between the Androgen Receptor and the Co-activator, Tif2, in Live Cells using Two Color, Two Photon Fluorescence Cross-correlation Spectroscopy," European Biophysics Journal, 2007, vol. 36 (2), pp. 153-161.

Ruan Q., et al., "Applications of Dual-color Fluorescence Cross-correlation Spectroscopy in Antibody Binding Studies," Analytical Biochemistry, 2008, vol. 374 (1), pp. 182-195.

International Preliminary Report on Patentability and Written Opinion for Application No. PCT/US2012/040925, dated Dec. 27, 2013, 8 pages.

European Patent Office Extended Search Report for Application No. 16198871.2 dated Jan. 18, 2017 (9 pages).

\* cited by examiner

SPATIALLY RESOLVED LIGAND-RECEPTOR BINDING ASSAYS

BACKGROUND OF THE INVENTION

1. Field of the Invention

This invention relates to determination of the concentration of a ligand in a sample, more particularly, a ligand that specifically binds to a receptor.

2. Discussion of the Art

For the past several decades, immunoassays have been performed using fluorescence, chemiluminescence, or other means of generating a signal in response to an analyte. Currently, many immunoassays are performed by measurement of the intensity of a light signal generated in the total volume of a reaction mixture. The light signal generated can be measured by an optical means, wherein the light signal generated is emitted by a large number of molecules. In a typical embodiment, these immunoassays can be carried out by combining a sample suspected of containing an antigen with a reagent comprising a first antibody attached to a solid support, e.g., a bead, a microparticle, to form a reaction mixture. The antigen, if present in the sample, specifically binds to the first antibody. A conjugate, which comprises a second antibody having a label attached thereto, is introduced to the reaction mixture and specifically binds to the antigen, which is specifically bound to the first antibody, which, as stated previously, is attached to the solid support. Such an immunoassay is referred to as a sandwich immunoassay or an immunometric assay. This type of immunoassay is shown schematically in FIG. 1. The signal attributable to the label is then measured after unbound conjugate is removed from the reaction mixture, typically by performing a wash step. The signal that is derived from the total volume of the reaction mixture is measured and then compared to a calibration curve to establish the concentration of antigen present in the sample.

Another type of immunoassay is called a competitive immunoassay. In a typical embodiment, an unlabeled antigen and a labeled antigen compete for the same antibody site. Alternatively, an antibody and a labeled antibody compete for the same antigen site. In an example of the former, a labeled antigen and an unlabeled antigen are used. A solid support is coated with an antibody that can specifically bind to either the labeled antigen or to the unlabeled antigen. The solid support, the labeled antigen, and a patient's sample suspected of containing the antigen are combined. Of course, any antigen in the patient's sample is unlabeled. The labeled antigen and the unlabeled antigen compete for antibody sites on the solid support. Only when the labeled antigen attaches to the antibody on the solid support can a signal be produced, because only the labeled antigen can generate a signal. The amount of antigen in the patient's sample is inversely proportional to the amount of signal produced. This type of immunoassay is shown schematically in FIG. 2.

In performing immunoassays using different optical methods, a number of parameters must be considered. These parameters include the time required to perform the immunoassay, the amount of sample needed to carry out the immunoassay, the amount of additional reagents needed to carry out the immunoassay, the number of steps needed to complete the immunoassay, the sensitivity of the immunoassay, and the dynamic range of the immunoassay. The dynamic range can often cover three or more orders of magnitude. For many decades, immunoassays that utilize magnetic microparticles have been shown to provide adequate values for most of the parameters mentioned previously. Magnetic microparticles allow separation of analyte bound to conjugate from unbound conjugate and other reagents in a simple manner. Another attractive property of magnetic microparticles is that they can easily be controlled in a solution in order to allow for binding of analyte or conjugate in the solid phase in a relatively short time. By making use of magnetic attraction, magnetic microparticles can be moved and washed in order to provide information about only the analyte bound to the magnetic microparticles.

A major drawback with the use of any microparticle as the solid support is lack of uniformity from microparticle to microparticle with respect to the amount of antibody coated on the microparticle. Another drawback is the undesired interaction of the conjugate with the microparticles. Such undesired interaction may affect results of the immunoassay and, consequently, may require extensive study of a number of different microparticles, made by different manufacturers, for use on an immunoassay analyzer. Another drawback presents itself when immunoassays are performed in a reaction vessel. The conjugate can bind to the surfaces of the reaction vessel, which is undesirable. These drawbacks not only limit sensitivity of an immunoassay, but can yield false results upon measurement of the analyte.

Additional problems that may arise in immunoassays involve (a) non-specific binding of the conjugate to the solid support and (b) aggregation of reagents. These problems are a major concern to developers of an assay. Typically, methods to reduce non-specific binding involve not only tailoring of reagents, but also mixing them in appropriate proportions to provide the desired results. These methods, which entail a significant amount of trial and error, often result in making development of an assay a long process, as well as making development of an assay an empirical process, with the result that reagents often vary from one lot to another lot. Moreover, a signal resulting from non-specific binding of the conjugate can be higher than the signal resulting from specific binding of the conjugate to an analyte, thereby limiting the sensitivity of the immunoassay. Only through the use of calibration using samples free of any analyte can the effects of non-specific binding during an actual assay be estimated.

Another potential drawback of a typical immunoassay is that after the assay is performed, the only record of the assay is the value of signal. There is no opportunity to recheck the sample for defects or to obtain more information if new methods of analysis become available. Not only will there be no record of the properties of the solid phase, there will also be no way to review recorded data using a newly developed algorithm. The ability to use historical data in order to extract new information is not possible.

Therefore, a need exists to develop analytical instruments and methods for addressing non-specific binding and undesired performance of the solid phase in a given assay while simultaneously acquiring data from the assay to improve sensitivity of the assay. A need exists to reduce use of reagents and provide measurement in an adequate time for use in both a laboratory setting and a point-of-care setting. In principle, such a method would also provide real-time quality control as the assay is being performed. Furthermore, it is desired to alleviate the need to generate new calibration curves and to reduce the variation of reagents from lot to lot. It would also be desirable to maintain a record of the assay in such a manner that it can be reviewed at a later date through the use of different methods as these methods become available.

New detection methods can be coupled with devices from the emerging fields of nanotechnology and microfluidics to provide smaller, more effective, and more sensitive assays for detecting and measuring analytes in biological samples.

SUMMARY OF THE INVENTION

This invention provides a method for analyzing a ligand-receptor binding assay comprising the steps of:
(a) qualifying at least one signal of a ligand-receptor binding assay; and
(b) providing the results of the ligand-receptor binding assay.

More particularly, the ligand-receptor binding assay involves combining appropriate reagents in which receptors attached to a solid support, such as, for example, a microparticle, a sample suspected of containing a ligand, such as, for example, an analyte, and a conjugate comprising a label form a complex in which the label is present at a concentration that is directly proportional to the amount of ligand present in the sample. The label of the conjugate is attached to a second receptor, which is different from the receptor attached to the solid support. Alternatively, the ligand-receptor binding assay involves combining appropriate reagents to perform a ligand-receptor binding assay in which receptors attached to a solid support, such as, for example, a microparticle, a sample suspected of containing a ligand, such as, for example, an analyte, and a conjugate comprising a label form a complex in which the label is present at a concentration that is inversely proportional to the amount of analyte present in the sample. The label of the conjugate is attached to a ligand, which is the same ligand as the ligand suspected of being in the sample. In order to improve the sensitivity of the immunoassay, an optional reaction step and an optional washing step can be employed to reduce non-specific binding and remove any excess of conjugate. Another alternative is a one-step homogeneous immunoassay, which does not require a separation step.

In one embodiment, microparticles bearing receptors on the surface thereof, a sample suspected of containing an analyte, i.e., the ligand, and a conjugate comprising a label attached to a second receptor, in which the second receptor differs from those receptors attached to the microparticles, are introduced into a reaction vessel and allowed to react, whereby a complex comprising a label that emits a light signal is formed. The reaction vessel is capable of allowing the complexes comprising the labels that emit light signals to be recorded in an image. The resulting image is capable of being stored for use at a later time. The light signal from the image is qualified before being used as a measurement of the concentration of an analyte. The image includes a number of pixels, and the image is qualified and quantified on a pixel-by-pixel basis.

Qualification involves restricting the analysis to those portions of the image where complexes are located and measuring the value of intensity of light emanating from complexes in the image. An algorithm that is suitable for qualifying a light signal from a complex in an image comprises the steps of:
(a) acquiring a first fluorescence image to determine the location of a first conjugate in the complex;
(b) selecting pixels in the image for analysis;
(c) calculating and recording the average and variance of counts per pixel for the pixels selected in step (b);
(d) omitting from the analysis pixels that have counts greater than or less than a specified level of variance; and
(e) calculating the average of counts per pixel of the remaining pixels.

From the data obtained in step (e), the concentration of an analyte in a sample can be determined.

In an optional step, a white light image of the reaction mixture can be obtained to determine the location of complexes attached to a solid support. In another optional step, a second fluorescence image can be acquired to determine the location of a second conjugate in the complex. The second fluorescence image can be used to increase sensitivity with respect to determining the concentration of an analyte in a sample.

With respect to sandwich immunoassays, the receptor attached to the solid support is often referred to as a capture antibody. The second receptor, which is attached to the label is often referred to as a detection antibody. The reaction vessel can be a micro-well of a micro-well plate. In a typical sandwich immunoassay, after the reaction mixture is allowed to incubate for a prescribed period of time, the reaction mixture is typically washed to remove any excess of detection antibody and other unbound substances. The complex that remains in the reaction vessel is then imaged by, for example, a fluorescence microscope equipped with a digital camera. The average value of light intensity per pixel is then determined. The value thus determined can then be used to determine the concentration of antigen in the sample.

With respect to certain types of competitive immunoassays, the receptor attached to the solid support can also be deemed a capture antibody. However, when an antigen attached to a label, and the sample is suspected of containing the antigen, this particular type of competitive immunoassay does not have a detection antibody. The reaction vessel can be a micro-well of a micro-well plate. In this particular type of competitive immunoassay, after the reaction mixture is allowed to incubate for a prescribed period of time, the reaction mixture is typically washed to remove the excess of labeled antigen and any other substances remaining in the reaction mixture. The material remaining in the reaction vessel is then imaged by, for example, a fluorescence microscope equipped with a digital camera. The average value of light intensity per pixel is then determined. The value determined is then used to determine the concentration of antigen in a sample. As indicated previously, there are other types of immunoassays that can be carried out to provide the results needed to carry out the imaging aspects of this invention.

In another embodiment, the ligand can be single strand of nucleic acid, e.g., DNA, RNA, and the receptor can be complementary strand of nucleic acid, e.g., DNA, RNA. In this embodiment, the ligand-receptor binding reaction can be used to identify the presence of a gene or specific nucleic acid sequence, e.g., DNA sequence, RNA sequence.

An alternative method for providing additional information relating to the aforementioned ligand-receptor binding assays involves counting of the number of microparticles or fluorescent spots that meet or exceed at least one selected criterion for calculation of intensity. This alternative method can provide an internal control for indicating proper performance of the assay. In principle, comparison of results from assay to assay can be performed to ensure that each assay is reliable, i.e., sufficiently sensitive and sufficiently precise. The average value of fluorescence intensity per microparticle can be used to determine the concentration of a ligand, in contrast to the value of intensity per pixel. The two values should both agree with values from the calibrator, thereby yielding two statistical measures that can be used to determine concentration of an analyte.

The method described herein also enables maintaining a record of the assay in a manner similar to those in which x-rays and tissue pathology records are maintained. Because images are acquired and stored off-line, i.e., by way of computer data storage that is not available for immediate use on demand by the system without human intervention, different procedures for analysis can be employed at a later date. A benefit of this feature is the enablement of direct comparison of assay results from samples taken from the same patient at different times. In this manner, information about an actual sample and assays thereof is not lost and can be shared or reviewed at a later time.

The method described herein addresses problems inherent in measurement of total signal by generating fluorescence images of complexes comprising microparticles after a ligand-receptor binding assay is performed. In the method described herein, measurement of intensity of light emitted from the total volume of a sample is replaced by analysis of images of the complex comprising an analyte from the sample in order to improve the sensitivity of the assay. By incorporating spatial information that is not contained in conventional ligand-receptor binding assays, aggregation of reagents and non-specific binding can be eliminated from the signal generated and the analyte in the sample can be qualified and simultaneously or subsequently quantified. For example, with respect to qualification, undesired artifacts associated with a solid phase, such as, for example, microparticles, can be examined and removed before the use of intensity information. Alternatively, if it is desired that the degree of aggregation of proteins be measured, the aforementioned spatial information relating to aggregation can be measured, rather than removed from the signal generated. For example, aggregation of amyloids is an indicator of Alzheimer's disease. Furthermore, with respect to quantification, the method described herein allows the omission of intensity information from reagents and conjugates that have non-specifically bound to the wall of a reaction vessel and from reagents and conjugates diffusing in the reaction mixture. Spatial information can be used to precisely define the region in an image from which intensity should be measured in order to perform a precise and accurate ligand-receptor binding assay.

Conventional assays require a large quantity of sample and a large quantity of reagent to provide sufficient signal. The method described herein requires only a small amount of a solid support material, such as, for example, only a few hundred coated microparticles, e.g., up to about two hundred (200) microparticles, or fewer. The method described herein enables the rechecking of samples for defects or to obtain more information if new methods of analysis become available.

BRIEF DESCRIPTION OF THE DRAWINGS

FIG. 8 was generated by a software program.

In FIG. 11, the average value of fluorescence intensity per pixel from the total area of the image for each calibrator is also shown.

FIG. 14 was generated by a software program.

DETAILED DESCRIPTION

As used herein, the term "analyte" means a compound or composition to be measured, which may be a ligand, which is monoepitopic or polyepitopic, antigenic or haptenic, a single or plurality of compounds, which share at least one common epitopic site or a receptor.

An immunoassay is a biochemical test that measures the presence or concentration of a substance in solutions that frequently contain a complex mixture of substances. Analytes in biological liquids such as serum or urine are frequently assayed using immunoassay methods. Such assays are based on the unique ability of an antibody to bind with high specificity to one or a very limited group of molecules. A molecule that binds to an antibody is called an antigen. Immunoassays can be carried out for either member of an antigen/antibody pair. In addition to binding specificity, the other key feature of all immunoassays is a means to produce a measurable signal in response to a specific binding. Historically this was accomplished by measuring a change in some physical characteristic such as light scattering or changes in refractive index. Nevertheless most immunoassays today depend on the use of an analytical reagent that is associated with a detectable label. A large variety of labels have been demonstrated including enzymes; fluorescent, phosphorescent, and chemiluminescent dyes; latex and magnetic particles; dye crystalites; gold, silver, and selenium colloidal particles; metal chelates; coenzymes; electroactive groups; oligonucleotides, stable radicals, and others. Such labels serve for detection and quantitation of binding events either after separating free and bound labeled reagents or by designing the system in such a way that a binding event effects a change in the signal produced by the label. Immunoassays requiring a separation step, often called separation immunoassays or heterogeneous immunoassays, are popular because they are easy to design, but they frequently require multiple steps including careful washing of a surface onto which the labeled reagent has bound. Immunoassays in which the signal is affected by binding can often be run without a separation step. Such assays can frequently be carried out simply by mixing the reagents and sample and making a physical measurement. Such assays are called homogenous immunoassays or less frequently non-separation immunoassays.

Figure 1:
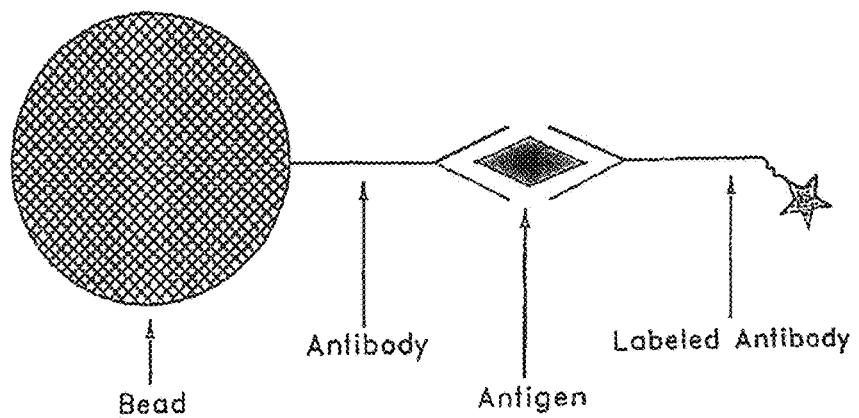
FIG. 1 is a schematic diagram illustrating a sandwich immunoassay.

As used herein, the expression "sandwich immunoassay" means an immunoassay that employs at least two receptors that specifically bind to the same ligand. In this type of immunoassay, the ligand is the analyte. One of the receptors is capable of specifically binding to the ligand, whereby the receptor enables the ligand to be attached directly or indirectly to a solid support, such as, for example, a microparticle. The other receptor is capable of specifically binding to the ligand, whereby the receptor enables the ligand to be attached directly or indirectly to a label to provide a signal for detecting the ligand. For example, one of the receptors can be a capture antibody for specifically binding to an antigen in a sample, whereby the antigen is attached directly or indirectly to a solid support, such as, for example, a microparticle, and the other receptor can be a detection antibody for specifically binding to the antigen in the sample, whereby the antigen is attached directly or indirectly to a label for detecting the antigen. If a relatively high amount of ligand is present in the sample, a higher signal will be produced. If a relatively low amount of ligand is present in the sample, a lower signal will be produced. FIG. 1 is a schematic diagram illustrating a representative example of a sandwich immunoassay.

Figure 2:
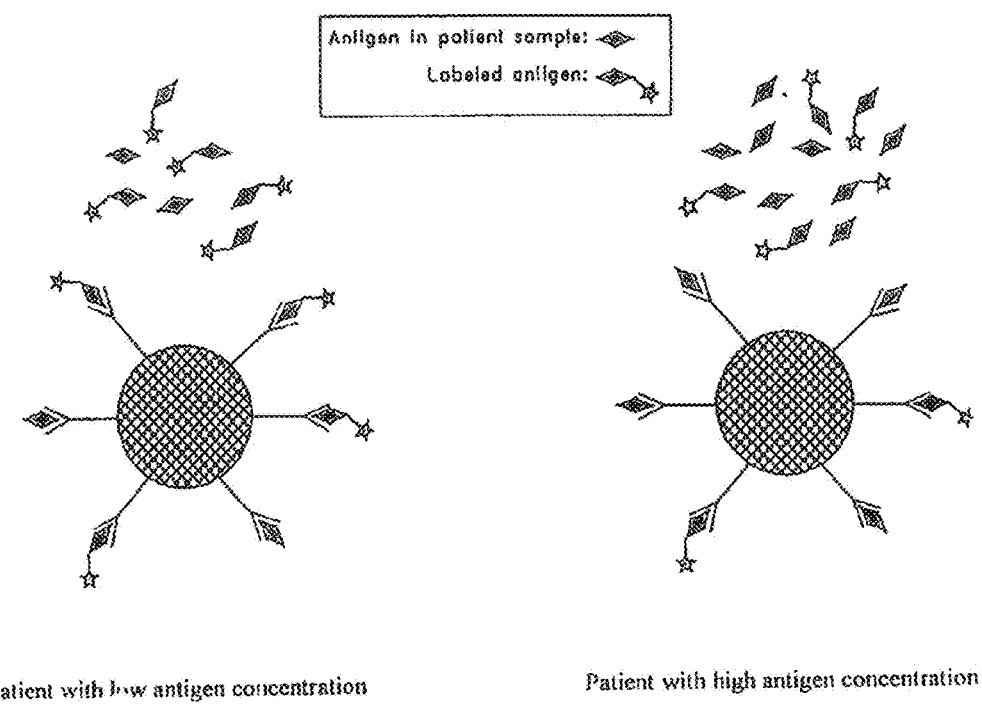
FIG. 2 is a schematic diagram illustrating a competitive immunoassay.

As used herein, the expression "competitive immunoassay" means an immunoassay that employs a receptor that binds to a ligand. In this type of immunoassay, the ligand is the analyte. The receptor is capable of specifically binding to the ligand, whereby the ligand is attached directly or indirectly to a solid support, such as, for example, a microparticle. A labeled ligand competes for the same receptor as does the analyte. For example, the receptor can be a capture antibody for specifically binding to an antigen in a sample, whereby the antigen is attached directly or indirectly to a solid support, such as, for example, a microparticle. The antigen in the sample is unlabeled. A labeled antigen competes for the same capture antibody as does the unlabeled antigen. The labeled antigen that becomes attached to the solid support provides a label for detecting the antigen. Alternatively, in the case where the receptor is an antigen for specifically binding to an antibody in a sample, whereby the antibody is attached directly or indirectly to a solid support, such as, for example, a microparticle, an unlabeled antibody and a labeled antibody can compete for the same antigen. The labeled antibody that becomes attached to the solid support provides a label for detecting the antibody. If a relatively high amount of ligand is present in the sample, a lower signal will be produced. If a relatively low amount of ligand is present in the sample, a higher signal will be produced. FIG. 2 is a schematic diagram illustrating a representative example of a competitive immunoassay.

As used herein, the term "complex" means at least two molecules that are specifically bound to one another. Examples of complexes include, but are not limited to, a ligand bound to a receptor, a ligand bound to a plurality of receptors, e.g., a ligand bound to two receptors, a receptor bound to a plurality of ligands, e.g., a receptor bound to two ligands.

As used herein, the expression "solid phase" means that state of a receptor wherein the receptor is attached to a surface of a solid support such that the receptor cannot break free from the solid support in a liquid medium. A solid phase can easily be separated from a liquid in which the solid phase is dispersed. An example of a solid support to which a receptor can be attached is a microparticle, such as, for example, a magnetic microparticle. The microparticle can easily be separated from a liquid in which it is dispersed. The microparticle is readily dispersed in an aqueous medium.

As used herein, the expression "solid support" means a substance that is instrumental in creating a solid phase. Representative examples of solid supports, include but are not limited to, microparticles, micro-wells of micro-well plates, nanoparticles, gels, colloids, biological cells.

As used herein, the expression "capture antibody" means an antibody that binds an analyte, i.e., an antigen, to a solid support, with the result that the antibody attaches the analyte to the solid support, whereby the analyte is attached to the solid support either directly or indirectly through an intervening moiety or intervening molecule.

As used herein the expression "detection antibody" means an antibody that is attached to a moiety or to a molecule that provides or can be made to provide a detectable signal in a chemical or biological reaction.

As used herein, the expression "specific binding pair" means two different molecules, where one of the molecules has an area on the surface or in a cavity which specifically binds to a particular spatial organization of the other molecule. The members of the specific binding pair are referred to as ligand and receptor. As used herein, the expression "non-specific binding" means binding between two or more entities, such as, for example, two molecules, in a manner other than that which results in a specific binding pair.

As used herein, the term "ligand" means any substance for which a receptor naturally exists or can be prepared. Such substances include, but are not limited to, organic compounds, inorganic compounds, and chemical elements, e.g., copper, lithium.

As used herein, the term "receptor" means any compound or composition capable of recognizing a particular spatial and polar organization of a molecule, i.e., epitopic site. Illustrative receptors include naturally occurring receptors, e.g., thyroxine binding globulin, antibodies, enzymes, Fab fragments, lectins, and the like.

Binding of a ligand to a receptor involves non-covalent interaction between two molecular species. Typically, but not necessarily, a smaller ligand is a soluble molecule that binds to a larger receptor. Examples of binding of a ligand to a receptor include, but are not limited to, the following:

(a) a long single strand DNA receptor having a complementary sequence for a short single strand DNA ligand;
(b) any antibody receptor that binds to its complementary antigen ligand or antigen receptor that binds to its complementary antibody ligand;
(c) the intrinsic factor protein receptor that binds the vitamin $B_{12}$ ligand;
(d) the hemoglobin receptor for the oxygen molecule ligand.

As used herein, the term "conjugate" means an entity comprising a binding pair member and a member of a signal producing system, e.g., a label. As used herein, the term "label" means a member of a signal producing system which is directly or indirectly bonded to a binding pair member or to a microparticle. As used herein, the expression "signal producing system" refers to a system having one or more components, at least one component being conjugated to a specific binding pair member. The signal producing system produces a measurable signal which is detectable by external means, usually the measurement of electromagnetic radiation, and depending on the system employed, the level of signal will vary to the extent the signal producing system is in the environment of the solid support, e.g., a microparticle. For the most part, the signal producing system will involve chromophores, where chromophores include dyes which absorb light in the ultraviolet or visible region, phosphors, fluorescers, fluorophores, luminophores, and chemiluminescers. In addition, enzymes can be employed to produce a signal or to amplify a signal or both of the foregoing.

As used herein, the terms "qualify", qualified", and the like refer to a procedure for removing those signals from an image that are not attributable to complex comprising the analyte of interest. Such signals that are removed include, but are not limited to, signals arising from non-specific binding, undesired aggregation, or signals that emanate from locations that are not attached to the solid support. In most cases, but with a few exceptions, those signals that qualify for analysis and measurement are the result of specific binding of a conjugate that comprises a label.

As used herein, and in the field of digital imaging in general, the term "pixel", or "pel" (picture element), means a single point in a digital image, or the smallest addressable screen element in a display device. It is the smallest unit of picture that can be represented or controlled. Each pixel has its own address. The address of a pixel corresponds to its spatial coordinates. Pixels are usually arranged in a two-dimensional grid, and are often represented using dots or squares. Each pixel is a sample of an original image; more samples typically provide more accurate representations of the original. The intensity of each pixel is variable. The total number of pixels in an image can vary. A representative example of the number of pixels in a digital image is 1024×1024.

As used herein, the term "intensity" means the amount or degree of strength of electricity, light, heat, or sound per unit area or volume. More particularly, with respect to the method actually described herein, the term "intensity" refers to the number of photons counted per unit of area per unit of time. For example, 1000 photons per unit area may be recorded as 500 counts in a single pixel, while 80 photons per unit area are recorded as 40 counts in a single pixel. The particular conversion depends on the camera system used. Intensity is proportional to the number of photons counted.

As used herein, the expression "region of interest" refers to those pixels in an image that are selected for further analysis. In an image, pixels can be contiguous or non-contiguous.

As used herein, the phrase "spatial information" means identification of a location from which a signal emanates.

As used herein, the term "IgG" means Immunoglobulin G.

In a general statement of the invention described herein, a ligand specifically binds to a receptor to form a ligand-receptor complex. An image is obtained of the ligand-receptor complex. The image is preferably stored so that it can be used at a later time, if desired. A region of interest is selected from the image in such a manner that only the ligand-receptor complexes are studied further.

This selection feature ensures that background signals and non-specific binding signals are substantially eliminated from further analysis. The average number of counts of light per pixel in the region of interest is calculated.

Ligands that are amenable to the method described herein include, but are not limited to, those mentioned in U.S. Pat. No. 4,275,149, incorporated herein by reference. Receptors that are amenable to the method described herein include, but are not limited to, those mentioned in U.S. Pat. No. 4,275,149, incorporated herein by reference. Ligand-receptor complexes that are amenable to the method described herein include, but are not limited to, those mentioned in U.S. Pat. No. 4,275,149, incorporated herein by reference.

Receptors are typically attached to a solid support. A solid support suitable for use herein is a microparticle. Microparticles that are suitable for use with the method described herein include, but are not limited to, magnetic microparticles. The sizes of microparticles typically range from about 0.1 µm to about 100 µm. Commercially available microparticles are available in a wide variety of materials, including those made of ceramics, glass, polymers, and metals. Magnetic microparticle suitable for use in the method described herein are commercially available from Polymer Laboratories, a subsidiary of Agilent Technologies. Although the generally accepted definition of 0.1 µm to 100 µm complements the size definition of nanoparticles, there are other ways to define the size. General acceptance considers microparticles smaller than 100 nm to be nanoparticles. Any microparticle larger than 0.5 µm and anything smaller than 0.5 mm is considered to be a microparticle. In general, the size of microparticles suitable for use with the method described herein must be sufficiently large so that two microparticles can be resolved by the image system selected. The properties of the microparticles suitable for use with the method described herein, such as, for example, color, is a matter of choice. One of ordinary skill in the art can select the properties of the microparticles in order to fulfill requirements imposed by appropriate variations of the method.

Reaction vessels that are suitable for use with the method described herein include micro-well plates. It is preferred that the reaction vessel be of such a character that an image of the ligand-receptor complex can be made. It is preferred that the reaction vessel be transparent to electromagnetic radiation, typically in the ultraviolet and the visible range of the spectrum. Materials that are suitable for making a reaction vessel include glass, and polymeric materials. It is preferred that the material of the reaction vessel not be auto-fluorescent. However, the particular form or shape of the reaction vessel is not critical.

Reaction conditions for assays contemplated for use with the method described herein are not critical. Substantially the same conditions that are used with conventional immunoassays or other conventional specific binding reactions can be used. Such conditions include, but are not limited to duration of incubation, temperature range of incubation, number of washing steps, buffers and other non-reactive substances in the assays, and the like. In principle, any immunoassay designed for use as a chemiluminescent assay can be carried out by the method described herein through the use of a fluorescent label.

Imaging systems suitable for use in the method described herein can be any system capable of acquiring images such that individual microparticles can be resolved. Imaging devices suitable for use with the method described herein include, but are not limited to, light microscopes, scanning microscopes, fluorescence imaging scanners, and the like. Image file types that are suitable for use with the method described herein include, but are not limited to, JPEG/JFIF, GIF, BMP, TIFF, and FITS. Image file formats are described at Image file formats—Wikipedia, the free encyclopedia, which is accessible by means of Hypertext Transfer Protocol at the website en.wikipedia.org/wiki/image_file_formats, incorporated herein by reference, and FITS is described at FITS—Wikipedia, the free encyclopedia, which is accessible by means of Hypertext Transfer Protocol at the website en.wikipedia.org/wiki/FITS, incorporated herein by reference.

Duration of exposure during acquisition of the image is not critical. Exposure times suitable for use with the method described herein can be any exposure time that provides sufficient resolution for discerning relevant details of the image.

The selection of the region of interest is important. Through the use of a suitable computer program, the locations of individual microparticles are determined by means of contrast or some alternative criteria. The pixels associated with the microparticles or other solid support can be deemed a region of interest. In order to obtain a meaningful value of concentration of an analyte in a sample, it is preferred that at least about 100 microparticles, more preferably at least about 200 microparticles be located in an image. Commercially available computer programs suitable for use in the method described herein include, but are not limited to, those programs having the trademarks "SLIDEBOOK" and "METAMORPH" or software in the public domain, such as, for example, ImageJ.

In order to carry out a simplified form of the method, a commercially available epifluorescence microscope can be used to image the complexes through a transparent surface upon which they are supported. A representative example of such a microscope is a motorized inverted fluorescence microscope (OLYMPUS "IX81") coupled with a high resolution CCD camera (Hamamatsu Model C4742-80-12AG), which are commercially available from numerous sources.

In this basic form of the method, a single-color approach can be used to provide greater sensitivity than a conventional immunoassay employing a light signal from the total volume of a reaction mixture.

This greater sensitivity can be evidenced by a plot of a linear function having a greater slope at lower concentrations relative to that of a linear plot employed as a calibration curve in a conventional immunoassay.

Microparticles bearing capture antibodies, detection antibodies attached to fluorophores, and a sample suspected of containing an analyte are combined under appropriate conditions to carry out an immunoassay. After the immunoassay is carried out, any fluorescence signal that does not emanate from a complex comprising a microparticle attached to a capture antibody, an analyte, and a conjugate comprising a detection antibody attached to a fluorophore is omitted. Then, the complexes remaining are further qualified based on fluorescence emitted by the fluorophore of the conjugate. This latter step omits any sections on the surface of the microparticle that do not meet selection criteria. Based on a statistical parameter, such as, for example, standard deviation, a typical example of a selection criterion is that the microparticles to be used for measurement have a substantially homogeneous coating, which essentially eliminates excessive aggregation of conjugates, which can result from a high degree of non-specific binding. In general, selection criteria vary, depending upon the particular assay. One of ordinary skill in the art of the particular assay should be able to formulate meaningful selection criteria for that particular assay. Finally, the average value of intensity per pixel of the qualified particles is measured in order to compare the intensity to a calibration curve that establishes concentration of the analyte as a function of intensity. The average value of intensity per pixel of the qualified particles can be determined by means of a CCD camera, which is capable of measuring intensity of light. The measurement of intensity is converted to a parameter, which is designated in the units of counts. Each pixel has a number corresponding to the intensity of light measured at that pixel.

In a preferred embodiment, a white light image of the reaction mixture is obtained. The white light image is employed to locate the position of each solid support, e.g., a microparticle. A white light image is formed by using the entire electromagnetic spectrum for both illumination and detection. This step is not required, but is preferred because it may be desirable to locate the position of each solid support, e.g., a microparticle. A fluorescence image is then acquired to determine the location and intensity of detection antibodies attached to microparticles. The fluorescence image uses a color, e.g., red, green. Counts per pixel are calculated and the average and standard deviation of counts per pixel are recorded. Pixels that have counts greater than or less than, for example, two times the aforementioned standard deviation are omitted from the analysis. The average number of counts per pixel for the pixels remaining are calculated. The quantity of signal measured from the label of the detection antibody determines the concentration of the analyte.

In order to carry out a more sophisticated measurement that will provide a higher degree of sensitivity, a commercially available epifluorescence microscope can be used to image the complexes through a transparent surface upon which they are supported. A representative example of such a microscope is a motorized inverted fluorescence microscope (OLYMPUS "IX81") coupled with a high resolution CCD camera (Hamamatsu Model C4742-80-12AG), which are commercially available from numerous sources.

In this more sophisticated measurement, a dual-color approach is used to provide greater sensitivity than both a conventional immunoassay employing a light signal from the total volume of reaction mixture and a measurement made by the single-color approach described earlier. This greater sensitivity is evidenced by a plot of a linear function having a greater slope at lower concentrations relative to that of a linear plot employed as a calibration curve in a conventional immunoassay or an assay using the single-color approach.

Microparticles bearing capture antibodies, detection antibodies attached to fluorophores, and a sample suspected of containing an analyte are combined under appropriate conditions to carry out an immunoassay. After the immunoassay is carried out, any fluorescence signal that does not emanate from a complex comprising microparticle attached to a capture antibody, an analyte, and a conjugate comprising a detection antibody attached to a first fluorophore is omitted. Next, an image of the capture antibody (characterized by a second fluorophore, which is different from the first fluorophore) is obtained. This image omits any pixels corresponding to any microparticles that are not coated with capture antibody in a homogeneous manner. If a microparticle is not uniformly coated, pixels from that portion that is not uniformly coated are omitted. Then, the complex is further qualified based on fluorescence emitted by the conjugate. This latter step omits any sections on the complex that do not meet selection criteria. A typical example of a selection criterion is homogeneous coating, which essentially eliminates excessive aggregation of conjugates, which can result from a high degree of non-specific binding. As stated previously, selection criteria vary, depending upon the particular assay. Finally, the average value of intensity per pixel of the qualified particles is measured in order to compare the intensity to a calibration curve that establishes concentration of the analyte.

In a preferred embodiment, a white light image of the reaction mixture is obtained. The white light image is employed to locate the position of each solid support, e.g., a microparticle. A white light image is formed by using the entire electromagnetic spectrum for both illumination and detection. This step is not required, but is preferred because it may be desirable to locate the position of each solid support, e.g., a microparticle. A first fluorescence image is then acquired to determine the locations of the capture antibodies attached to microparticles. The first fluorescence image uses a color, e.g., red, green. A second fluorescence image is acquired to determine the locations of antibodies that are present as a component of a conjugate. The second fluorescence image uses a color, e.g., red, green, but the color of the second fluorescence image differs from the color of the first fluorescence image. Pixels derived from both a capture antibody on a microparticle and an antibody on a conjugate are selected for further analysis. Counts per pixel are calculated and the average and standard deviation of counts per pixel are recorded. Pixels that have counts greater than or less than, for example, two times the aforementioned standard deviation are omitted from the analysis. The average number of counts per pixel for the pixels remaining are calculated. The quantity of signal measured from the label of the detection antibody determines the concentration of the analyte.

Figure 3:
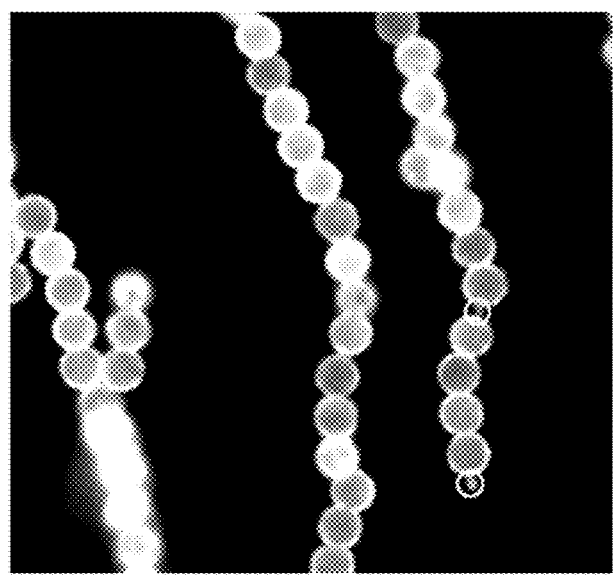
FIG. 3 is a fluorescence image of a capture antibody labeled with a red fluorophore.
Figure 4:
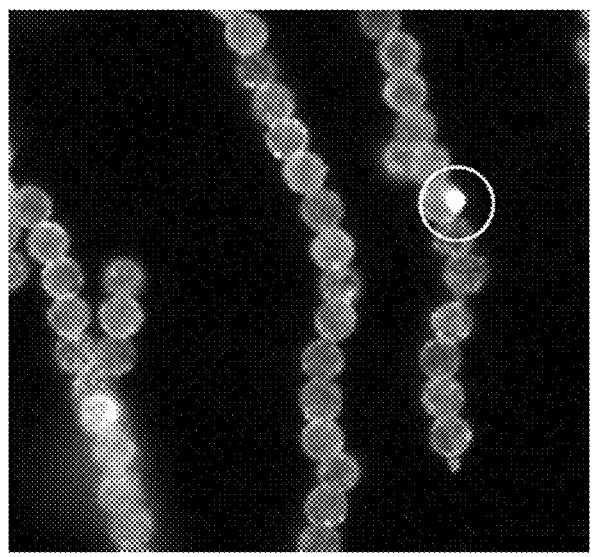
FIG. 4 is a fluorescence image of a detection antibody attached to a microparticle.
Figure 5:
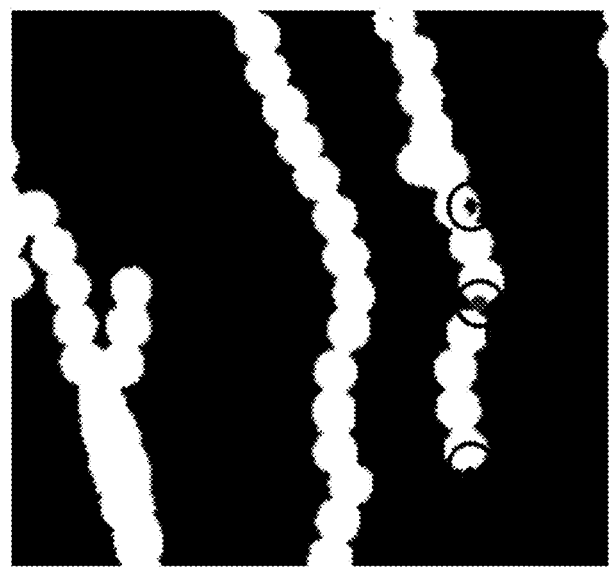
FIG. 5 is an image showing regions of interest from which the average intensity per pixel can be calculated.

FIGS. 3, 4, and 5 illustrate the steps required to qualify the results of a ligand-receptor binding assay. A fluorescence channel is defined with a set of filters comprising an excitation filter and an emission filter, which allows light having a specific wavelength to reach the sample and a signal having a specific wavelength to reach the CCD camera. For example, the fluorophore R-phycoerythrin (alternatively referred to herein as "PE") can only be detected in the PE channel and cannot be detected in any other fluorescence channel. Similarly, the fluorophore indodicarbocyanine (alternatively referred to herein as "Cy5") can only be detected in the Cy5 channel and cannot be detected in any other fluorescence channel. In FIG. 3, one channel of the detector measures the fluorescence image of a capture antibody, which was labeled with red fluorophores (Cy5 channel). Only microparticles that have been coated with capture antibody having the red fluorescent label appear. There are two locations (white circles) that may be omitted because they are not attached to the microparticle. In FIG. 4, another channel of the detector measures the fluorescence image of a detection antibody attached to the microparticle. A very bright spot that is not consistent with the intensity profile of the other microparticles appears and is designated with a white circle. This location may also be omitted from the analysis. FIG. 5 indicates the region of interest from which values of intensity per pixel can be calculated. Areas that did not meet given selection criteria can be omitted from this type of analysis.

The following non-limiting examples further illustrate embodiments of this invention. In the following examples, all concentrations are by weight (w/w) unless otherwise indicated. In the following examples, conjugates were prepared by conventional means known to those of ordinary skill in the art, unless otherwise indicated. In EXAMPLE 1, unless otherwise indicated, microparticles that bear a coating of anti-troponin monoclonal antibody 19C7 but which have not yet reacted in an immunoassay are referred to as "microparticles coated with anti-troponin monoclonal antibody 19C7"; microparticles that have reacted in an immunoassay and that are present in a sandwich complex are referred to as "microparticles attached to monoclonal antibody 19C7:troponin:conjugate M06-PE complex." In EXAMPLE 2, unless otherwise indicated, microparticles that bear a coating of anti-human IgG monoclonal antibody but which have not yet reacted in an immunoassay are referred to as "microparticles coated with anti-human IgG monoclonal antibody"; microparticles that have reacted in an immunoassay and that are present in a sandwich complex are referred to as "microparticles attached to conjugate 2322-Cy5:NGAL:conjugate 903-PE complex."

Example 1

This example illustrates an immunoassay for troponin, through the use of a single fluorescent dye as the label for the detection antibody.

Microparticles coated with anti-troponin monoclonal antibody 19C7 were prepared. A set of calibrators for troponin (TnI (28-110aa)-TnC) were prepared at the following concentration in phosphate buffered saline (PBS) containing bovine serum albumin (BSA) (0.5%), surface active agent ("STANDAPOL", 0.2%), and antimicrobial agent ("PROCLIN" 300, 0.1%). The following table lists the concentrations of Tn (28-110aa)-TnC in each calibrator.

TABLE 1

|  | Concentration of TnI (28-110aa)-TnC (pg/mL) |
| --- | --- |
| Calibrator A | 0 |
| Calibrator B | 10 |
| Calibrator C | 100 |
| Calibrator D | 500 |
| Calibrator E | 10,000 |
| Calibrator F | 50,000 |
| Low Control | 20 |
| Medium Control | 200 |
| High Control | 15,000 |

A conjugate comprising anti-troponin monoclonal antibody M06 and phycoerithrin (PE) was prepared by means of a R-PE conjugation kit (PJ31K, Prozyme Inc.) according to the protocol suggested therein. The conjugate is referred to herein as "conjugate M06-PE".

R-Phycoerythrin, or PE, is useful in the laboratory as a fluorescence-based indicator for labeling antibodies or other molecules in a variety of applications. R-Phycoerythrin absorbs strongly at about 566 nm with secondary peaks at 496 and 545 nm and emits strongly at 575 nm. R-Phycoerythrin is among the brightest fluorescent dyes ever identified. See, for example, Phycoerythrin—Wikipedia, the free encyclopedia, which is accessible by means of Hypertext Transfer Protocol at the website en.wikipedia.org/wiki/Phycoerythrin and R-PHYCOERYTHRIN (PB31), ProZyme Inc., Hayward, Calif., both of which are incorporated herein by reference.

Each calibrator (100 μL) was mixed with microparticles coated with anti-troponin monoclonal antibody 19C7 (2.5 μL, 0.1%) and the conjugate M06-PE (2 μL, 68 nM) in a 96 micro-well glass-bottom plate for 15 minutes at room temperature. The glass-bottom plate was used to reduce the level of auto-fluorescence. The 96 micro-well glass-bottom plate was then placed on a magnet ("DYNAL" "MPC"-96B) to attract the microparticles attached to monoclonal antibody 19C7:troponin:conjugate M06-PE complexes to the bottoms of the micro-wells during the wash step. In the wash step, phosphate buffered saline (100 μL) was added to each micro-well and then quickly removed. This step was repeated twice. Phosphate buffered saline (50 μL) was added to each micro-well after the final wash step, and the plate was placed on a motorized inverted fluorescence microscope (OLYMPUS "IX81") coupled with a high resolution CCD camera (Hamamatsu Model C4742-80-12AG). After the microparticles attached to monoclonal antibody 19C7:troponin:conjugate M06-PE complexes settled to the bottoms of the micro-wells, images of the microparticles attached to monoclonal antibody-antigen-monoclonal antibody complexes were taken with a UPlanSApo 20× objective (OLYMPUS) in the white light channel and the channel for the PE fluorophore. The viewing area of each image was approximately 400 micrometers×300 micrometers and usually had approximately 100 microparticles attached to monoclonal antibody 19C7:troponin:conjugate M06-PE complexes. A plurality of locations within a given micro-well was imaged to improve statistical analysis.

Figure 6:
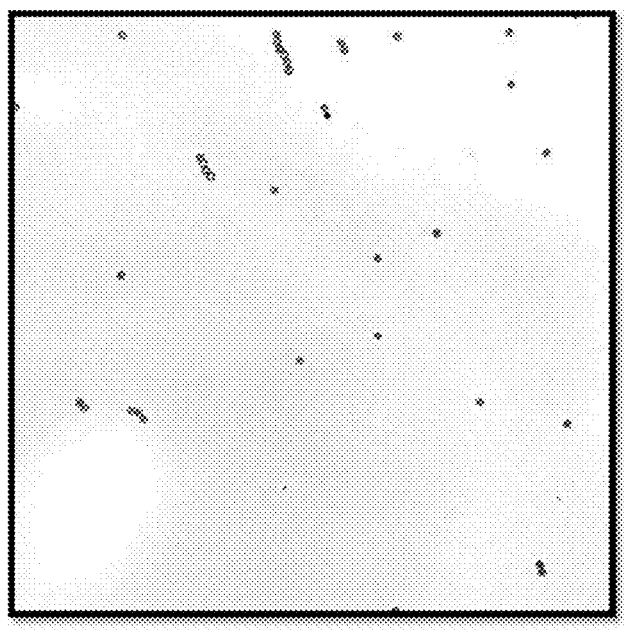
FIG. 6 is a white light image of microparticles having complexes of an antibody:analyte:conjugate (i.e., monoclonal antibody 19C7:troponin:conjugate M06-PE) attached thereto.

FIG. 6 shows white light images of the microparticles attached to monoclonal antibody 19C7:troponin:conjugate M06-PE complexes.

Figure 7:
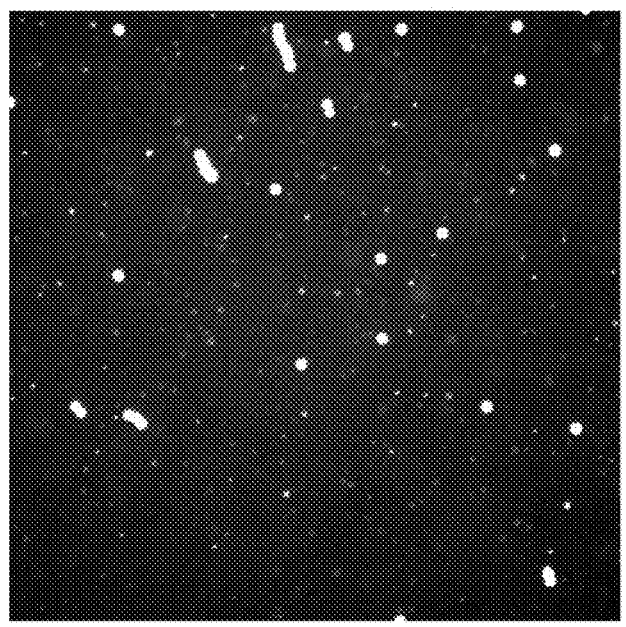
FIG. 7 is a fluorescence image of microparticles having complexes of an antibody:analyte:conjugate (i.e., monoclonal antibody 19C7:troponin:conjugate M06-PE) attached thereto.

FIG. 7 shows fluorescence images of the microparticles attached to monoclonal antibody 19C7:troponin:conjugate M06-PE complexes. The white light image was used to locate the position of each individual microparticle attached to a monoclonal antibody 19C7:troponin:conjugate M06-PE complex, based on the contrast of the individual microparticles attached to the monoclonal antibody 19C7:troponin:conjugate M06-PE complexes with the background.

Figure 8:
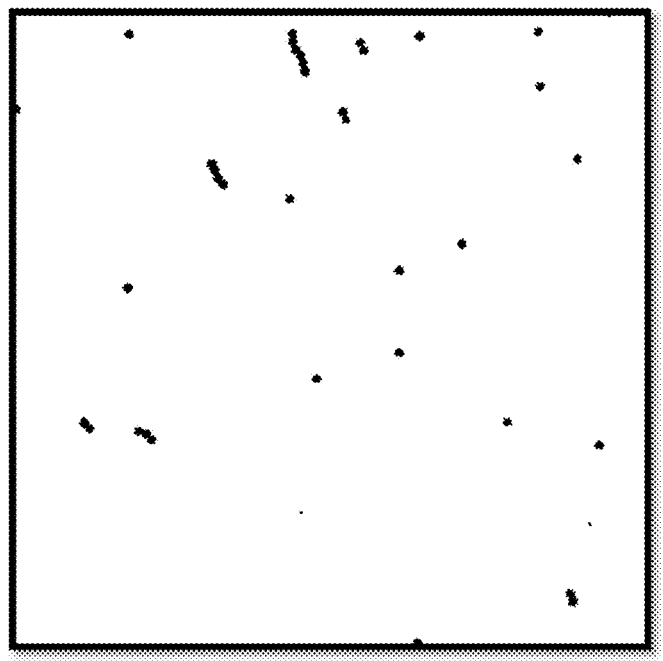
FIG. 8 is an image of the region of interest based on the images of FIG. 6 and FIG. 7.
Figure 9:
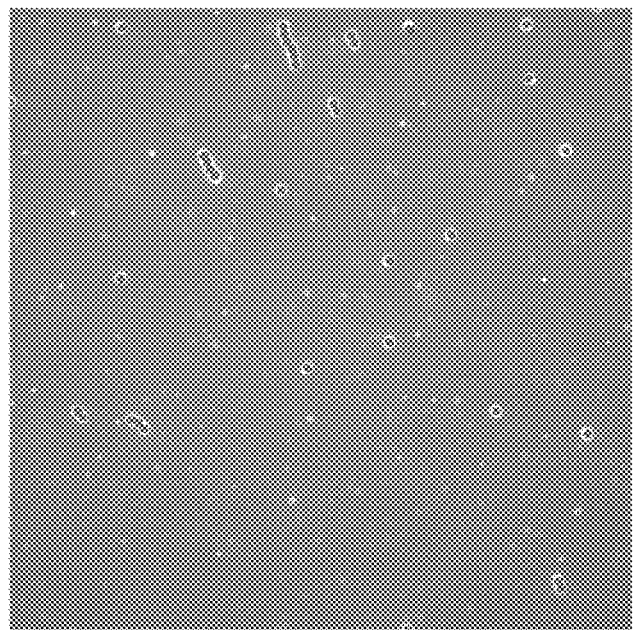
FIG. 9 is an overlay of the fluorescence image of FIG. 7 on the image of the region of interest of FIG. 8.
Figure 10:
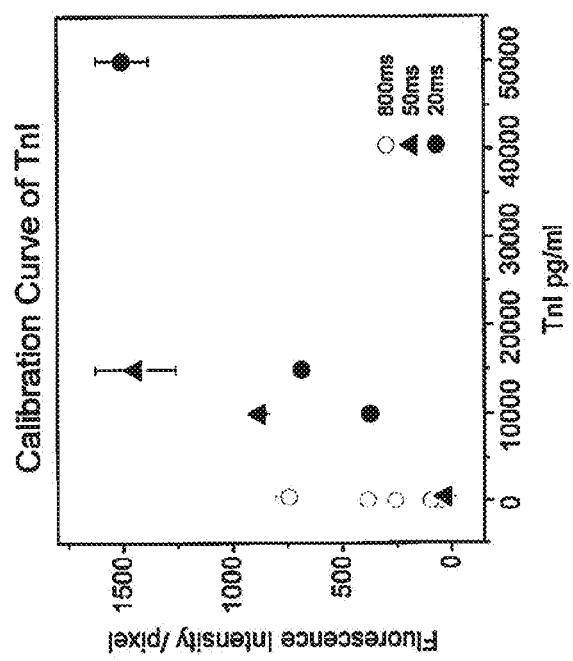
FIG. 10 is a calibration curve showing the increase in sensitivity of an immunoassay resulting from the use of an imaging algorithm described herein. For this calibration curve, the calibrators of the analyte (i.e., troponin) range from 10 pg/mL to 50,000 pg/mL.

FIG. 8 shows the locations of individual microparticles attached to monoclonal antibody 19C7:troponin:conjugate M06-PE complexes, which were defined as the region of interest. The region of interest comprises the light spots in FIG. 8. The average value of fluorescence intensity per pixel in the region of interest was then calculated using the digital image in the PE channel. In FIG. 9, there were spots substantially smaller than microparticles that did not overlap the region of interest. These spots of high fluorescence intensity emanated from the conjugates M06-PE that were not specifically bound to the surface of the micro-well plate. These spots were excluded from the analysis. The imaging and analysis approach described herein greatly reduced the background signals that did not emanate from the microparticles attached to monoclonal antibody 19C7:troponin:conjugate M06-PE complexes. The intensity values from all the calibrators were used to generate a calibration curve. On account of the limited dynamic range of the detector, a shorter exposure time was used for calibrators wherein concentrations of analyte are higher. FIG. 10 shows a calibration curve of calibrators ranging from 10 pg/mL to 50,000 pg/mL.

Figure 11:
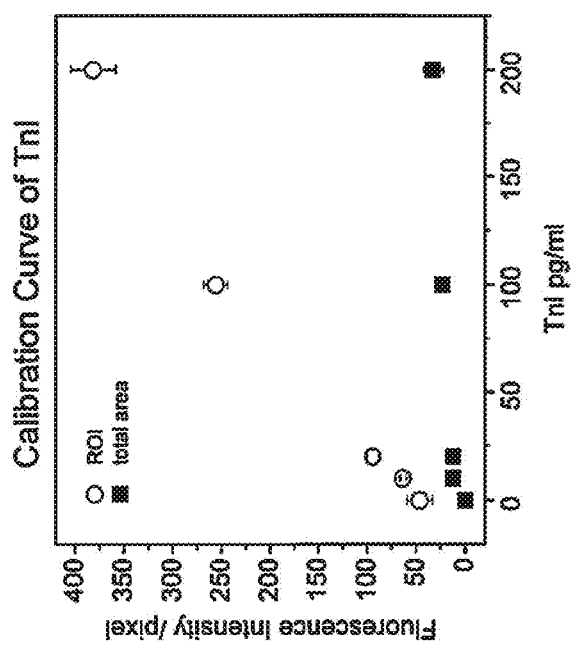
FIG. 11 is a calibration curve showing the increase in sensitivity of an immunoassay resulting from the use of an imaging algorithm described herein. For this calibration curve, the calibrators of the analyte (i.e., troponin) range from 0 pg/mL to 200 pg/mL.

FIG. 11 shows a zoomed-in calibration curve of calibrators ranging from 0 pg/mL to 200 pg/mL. In the zoomed-in graph, the average value of fluorescence intensity per pixel from the total area of the image for each calibrator was also plotted for comparison. It is evident that the use of spatial information of the image greatly increased the slope of the curve, thereby improving sensitivity of the immunoassay.

Example 2

This example illustrates an immunoassay for neutrophil gelatinase-associated lipocalin (alternatively referred to herein as "NGAL"), through the use of two fluorescent dyes, one as a label for the capture antibody, and the other as a label for the detection antibody.

Microparticles coated with anti-human IgG monoclonal antibody were prepared. A set of calibrators for neutrophil gelatinase-associated lipocalin ranging from 94 pM to 0.7 pM was prepared using HBS-EP buffer.

A conjugate comprising anti-NGAL monoclonal antibody 2322 and a fluorescent dye (Cy5) and a conjugate comprising anti-NGAL monoclonal antibody 903 and R-Phycoerythrin (PE) were prepared. Monoclonal antibody 2322 labeled with the Cy5 fluorophore is referred to herein as "conjugate 2322-Cy5". Monoclonal antibody 903 labeled with the PE fluorophore is referred to herein as "conjugate 903-PE."

Monoclonal antibody 2322 and monoclonal antibody 903 are monoclonal antibodies that can specifically bind to NGAL. Monoclonal antibody 2322 is a human chimeric antibody, and monoclonal antibody 903 is a mouse antibody. The microparticles coated with anti-human IgG monoclonal antibody can bind directly to monoclonal antibody 2322.

Cy5 is a reactive water-soluble fluorescent dye of the cyanine dye family. Cy5 is fluorescent in the red region of the electromagnetic spectrum (approximately 650 nm or 670 nm) but absorbs in the orange region of the electromagnetic spectrum (approximately 649 nm). Cy5 is also used to label proteins and nucleic acid for various studies including proteomics and RNA localization. See, for example, "Technical Information on Probes Conjugated to Affinity-Purified Antibodies and to Other Proteins: Cyanine Dyes (Cy2, Cy3, and Cy5)", which is accessible by means of Hypertext Transfer Protocol on the World Wide Web at the website jacsonimmuno.com/technical/f-cy3-5.asp, incorporated herein by reference.

The microparticles coated with anti-human IgG monoclonal antibody were blocked with monoclonal antibody 903. Because monoclonal antibody 903 is a mouse monoclonal antibody, it should not cross-react with microparticles coated with anti-human IgG monoclonal antibody. However, some cross-reactivity was found when the microparticles coated with anti-human IgG monoclonal antibody were incubated with monoclonal antibody 903 labeled with a PE fluorophore. If the microparticles coated with anti-human IgG monoclonal antibody are first treated with monoclonal antibody 903, and then reacted with monoclonal antibody 903 labeled with a PE fluorophore, the cross-reactivity of microparticles coated with anti-human IgG monoclonal antibody with monoclonal antibody 903 labeled with a PE fluorophore is greatly reduced. The average value of fluorescence intensity per pixel calculated from the region of interest in the images was 336 for microparticles coated with anti-human IgG monoclonal antibody when treated with conjugate 903-PE and 136 for microparticles coated with anti-human IgG monoclonal antibody first treated with monoclonal antibody 903 and then reacted with conjugate 903-PE. Additional runs showed that treating the microparticles coated with anti-human IgG monoclonal antibody with monoclonal antibody 903 does not decrease the signal generated from the analyte NGAL. When the concentration of NGAL is relatively high, the effect of the signal in the background of the image is not significant.

TABLE 2 shows fluorescence intensity of a sample containing 0 pM NGAL using (a) microparticles coated with anti-human IgG monoclonal antibody that were treated with monoclonal antibody 903 and (b) untreated microparticles coated with anti-human IgG monoclonal antibody. The intensity of the treated microparticles coated with anti-human IgG monoclonal antibody is approximately 40% that of the untreated microparticles coated with anti-human IgG monoclonal antibody.

TABLE 2

No NGAL in sample

|  | Average value of intensity per pixel for microparticles coated with anti-human IgG monoclonal antibody and treated with monoclonal antibody 903 (counts per pixel) | Average value of intensity per pixel for microparticles coated with anti-human IgG monoclonal antibody but untreated with monoclonal antibody 903 (counts per pixel) |
|---|---|---|
| Image 1 | 121.5 | 302.8 |
| Image 2 | 125.4 | 320.0 |
| Image 3 | 143.4 | 350.6 |
| Image 4 | 154.3 | 354.3 |
| Image 5 | 136.2 | 355.0 |
| Average | 136.2* | 336.5* |
| Standard deviation | 13.3 | 23.8 |

*dark counts from the camera are subtracted from the intensity

TABLE 3 shows the fluorescence intensity measured for a sample containing 300 pM NGAL using the microparticles coated with anti-human IgG monoclonal antibody that were treated with monoclonal antibody 903 and fluorescence intensity measured for a sample containing 300 pM NGAL using untreated microparticles coated with anti-human IgG monoclonal antibody. The immunoassay carried out for the purpose of determining the efficacy of using monoclonal antibody 903 as a blocking agent was conducted in the same manner as the immunoassays that were conducted to verify the concentration of NGAL. Images were measured with a shorter exposure time than that used for the images characterized in TABLE 1.

TABLE 3

300 pM NGAL in sample

|  | Average value of intensity per pixel for microparticles coated with anti-human IgG monoclonal antibody and treated with monoclonal antibody 903 (counts per pixel) | Average value of intensity per pixel for microparticles coated with anti-human IgG monoclonal antibody but untreated with monoclonal antibody 903 (counts per pixel) |
|---|---|---|
| Image 1 | 1491.8 | 1463.6 |
| Image 2 | 1513.7 | 1467.0 |
| Image 3 | 1520.5 | 1493.2 |
| Image 4 | 1521.2 | 1495.1 |
| Image 5 | 1535.6 | 1538.4 |
| Average | 1516.6 | 1491.4 |
| Standard deviation | 16.0 | 30.0 |

Microparticles coated with anti-human IgG monoclonal antibody (1 mL, 0.01%) were incubated with monoclonal antibody 903 (70 nM) for 15 minutes. The thus-treated microparticles coated with anti-human IgG monoclonal antibody were separated from the reaction mixture by means of a magnet and then washed with HBS-EP buffer. The thus-treated microparticles coated with anti-human IgG monoclonal antibody were then reconstituted to a concentration of 0.01% with HBS-EP buffer. In the first row of micro-wells of a micro-well plate having 96 micro-wells, various concentrations of NGAL (94 pM, 47 pM, 23 pM, 12 pM, 6 pM, 3 pM, 1.5 pM, 0.7 pM, 0 pM) were prepared. Each micro-well contained 100 μL of liquid. Monoclonal antibody 2322 labeled with Cy5 fluorophore (25 μL, 2 nM) and monoclonal antibody 903 labeled with PE fluorophore (8 μL, 20 nM) were added to the first row of micro-wells in the plate. The reaction mixtures were incubated for 15 minutes at room temperature. Microparticles coated with anti-human IgG monoclonal antibody (25 μL, 0.01%) were added to each micro-well in the first row. The reaction mixtures were incubated for an additional 20 minutes. The microparticles attached to conjugate 2322-Cy5:NGAL:conjugate 903-PE complexes were attracted to a magnet and then washed three times with HBS-EP buffer. The samples were transferred to a micro-well plate in which the micro-wells had glass bottoms. The micro-well plate was placed on the fluorescence microscope (OLYMPUS "IX81") and images were taken in the same manner as described in EXAMPLE 1 in the white light channel, in the PE channel, and in the Cy5 channel.

The white light image was used to locate the positions of individual microparticles attached to conjugate 2322-Cy5: NGAL:conjugate 903-PE complexes based on the contrast between the individual microparticles attached to conjugate 2322-Cy5:NGAL:conjugate 903-PE complexes and the background. The locations of individual microparticles attached to conjugate 2322-Cy5:NGAL:conjugate 903-PE complexes were defined as regions of interest. The regions of interest were further analyzed by setting a threshold in the Cy5 channel, whereby only those areas on the microparticles attached to conjugate 2322-Cy5:NGAL:conjugate 903-PE complexes having monoclonal antibody 2322 labeled with Cy5 fluorophore specifically bound to the microparticles attached to conjugate 2322-Cy5:NGAL:conjugate 903-PE complexes are used for further analysis. The average value of fluorescence intensity per pixel of the region of interest in the PE channel was calculated by means of a commercially available computer program ("SLIDEBOOK").

The following table lists the average value of intensity per pixel from the PE channel for each concentration of analyte at the corresponding duration of exposure. Three different durations of exposure were used to increase the dynamic range of the assay.

TABLE 4

| Exposure time (ms) | Number of microparticles | Concentration of NGAL (pM) | Average intensity per pixel (counts per pixel) | Standard deviation (counts per pixel) |
|---|---|---|---|---|
| 200 | 176 | 0 | 342 | 5 |
| 200 | 187 | 0.72 | 391 | 23 |
| 200 | 225 | 1.46 | 477 | 20 |
| 200 | 275 | 2.92 | 613 | 23 |
| 200 | 323 | 5.85 | 885 | 38 |
| 200 | 401 | 11.7 | 1625 | 90 |
| 200 | 342 | 23.4 | 2558 | 19 |
| 50 | 525 | 11.7 | 526 | 10 |
| 50 | 405 | 23.4 | 859 | 23 |
| 50 | 458 | 46.8 | 1294 | 95 |
| 50 | 342 | 93.75 | 1931 | 52 |

Figure 12:
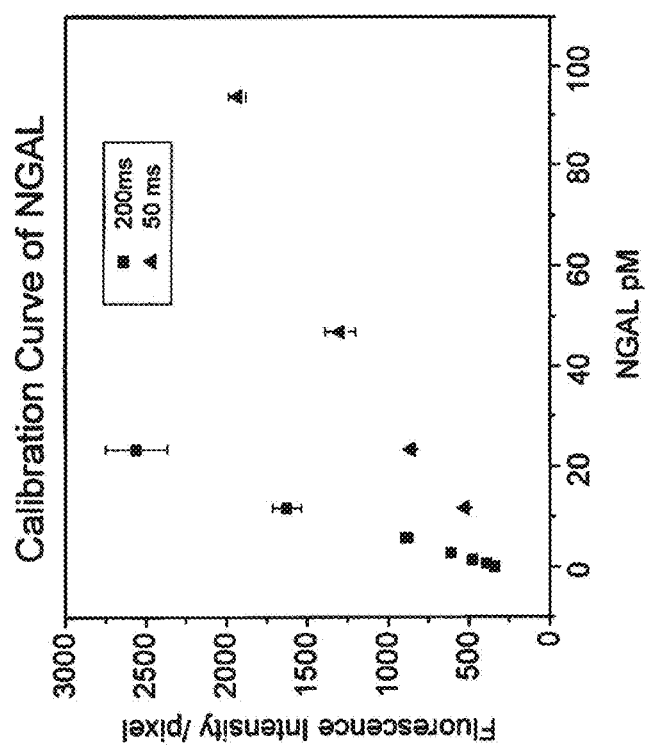
FIG. 12 is a calibration curve showing the average fluorescence intensity per pixel for calibrators of an analyte (i.e., neutrophil gelatinase-associated lipocalin, alternatively referred to herein as "NGAL"). For this calibration curve, the calibrators of the analyte NGAL range from 0 pM to 94 pM.
Figure 13:
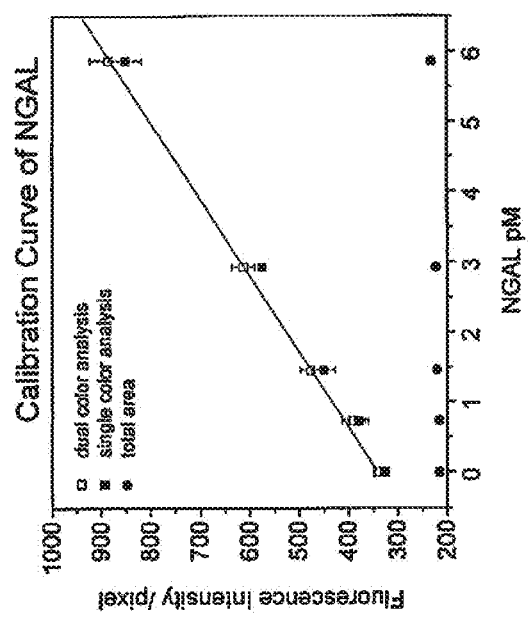
FIG. 13 is a calibration curve showing the average fluorescence intensity per pixel for calibrators of an analyte (i.e., neutrophil gelatinase-associated lipocalin, alternatively referred to herein as "NGAL"). For this calibration curve, the calibrators of the analyte NGAL range from 0 pM to 6 pM.

FIG. 12 shows calibration curves for NGAL generated from the data in TABLE 4. FIG. 13 shows the calibration curve at extremely low concentrations of calibrator. Three different algorithms were used to demonstrate the benefits of the present invention. Algorithm 2 and algorithm 3 greatly improved the sensitivity of the assay.

The data for Algorithm 1 appear as solid circles (●) in the graph. The average value of intensity of the entire image in the PE channel was calculated. No spatial information was used. This algorithm is equivalent to a measurement of total intensity.

The data for Algorithm 2 appear as solid squares (■) in the graph. All of the microparticles were selected as regions of interest using the white light image based on the contrast level. The dimensions of the regions of interest were reduced by setting a threshold in the PE channel. The cutoff was selected arbitrarily and was equal to the average value of fluorescence intensity of the image from the PE channel plus or minus three standard deviations. However, other cutoff values could have been used.

The data for Algorithm 3 appear as open squares (□) in the graph. An area on the microparticles attached to monoclonal antibody:antigen:monoclonal antibody complexes having intensity above a threshold in the Cy5 channel was selected, and then the average value of fluorescence intensity of the PE channel was calculated. Signals generated by non-specific binding were reduced. The cutoff was selected arbitrarily and was equal to the average value of fluorescence intensity of the image from the PE channel plus or minus three standard deviations. However, other cutoff values could have been used.

Example 3

Figure 14:
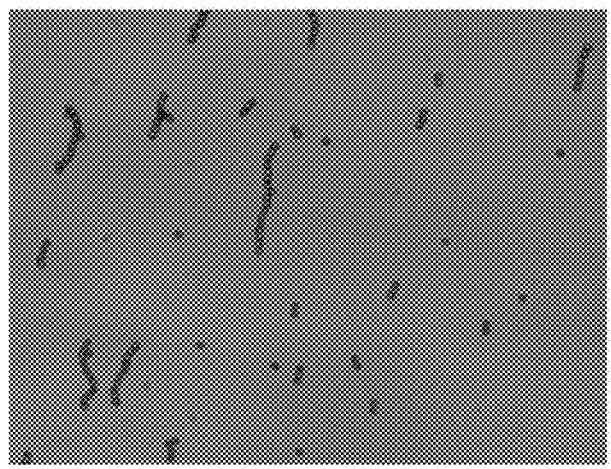
FIG. 14 is a white light image of microparticles having complexes of an antibody:analyte:conjugate (i.e., monoclonal antibody 19C7:troponin:conjugate M06-PE) attached thereto.
Figure 15:
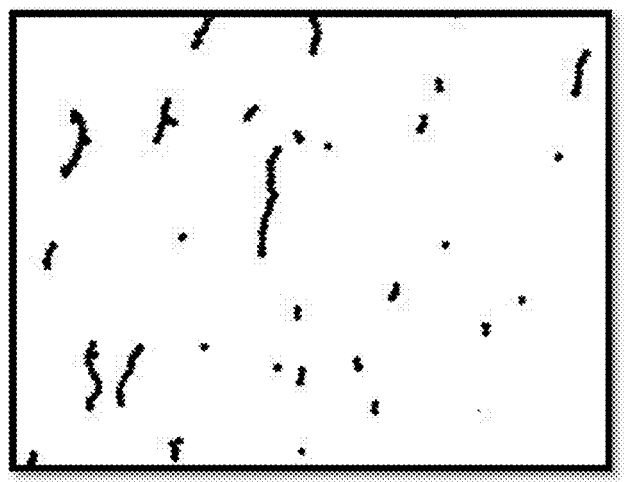
FIG. 15 is an image of a region of interest based on the image of FIG. 14.
Figure 16:
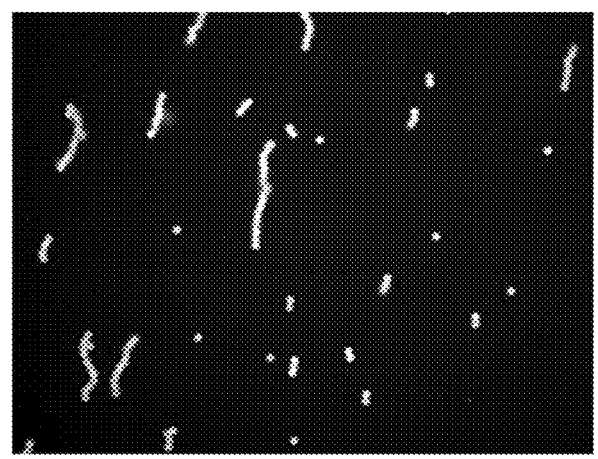
FIG. 16 is a fluorescence image of microparticles having complexes of antibody:analyte:conjugate (i.e., monoclonal antibody 19C7:troponin:conjugate M06-PE) attached thereto.
Figure 17:
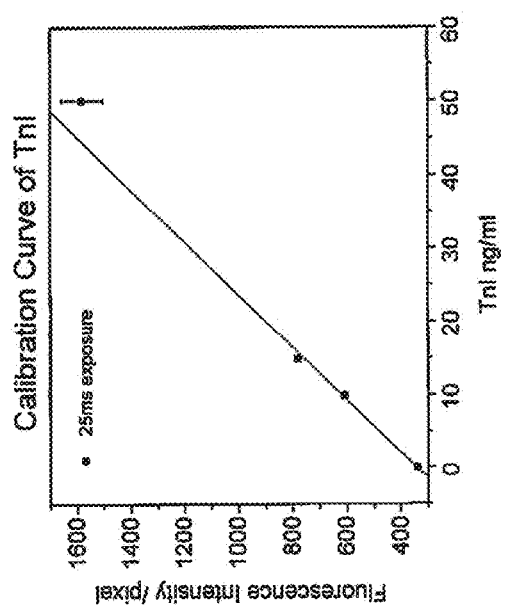
FIG. 17 is a calibration curve generated from the value of average intensity per pixel for each concentration of the calibrator troponin.

This example illustrates a homogeneous immunoassay for troponin, through the use of a single fluorescent dye as the label for the detection antibody. In some immunoassays, where the concentration of analyte is in the range of ng/mL, it is possible to perform a homogeneous immunoassay using the method described herein. Such immunoassays are carried out simply by mixing the reagents and sample and making a physical measurement. Homogeneous immunoassays are desirable because they are easy to perform. All reagents and imaging parameters used in this example were the same as those used in EXAMPLE 1. Each calibrator (100 µL) was mixed with microparticles coated with anti-troponin monoclonal antibody 19C7 (2 µL, 0.1%) and the conjugate M06-PE (5 µL, 20 nM) in a 96 micro-well glass-bottom plate for 15 minutes at room temperature. The glass-bottom plate was used to reduce the level of auto-fluorescence. Then PBS (200 µL) was added to each micro-well to lower the concentration of the conjugate and to reduce the fluorescence intensity of the background. The plate was placed on a motorized inverted fluorescence microscope (OLYMPUS "IX81") coupled with a high resolution CCD camera (Hamamatsu Model C4742-80-12AG). After the microparticles attached to monoclonal antibody 19C7:troponin:conjugate M06-PE complexes settled to the bottoms of the micro-wells, images of the those microparticles attached to monoclonal antibody 19C7:troponin:conjugate M06-PE complexes were taken with a UPlanSApo 20× objective (OLYMPUS) in the white light channel and the PE channel. The white light image, shown in FIG. 14, was used to locate the position of each individual microparticle attached to a monoclonal antibody 19C7:troponin:conjugate M06-PE complex, based on the contrast of the individual microparticles attached to the monoclonal antibody 19C7:troponin:conjugate M06-PE complexes with the background. FIG. 15 shows the locations of individual microparticles attached to monoclonal antibody 19C7:troponin:conjugate M06-PE complexes, which locations were defined as the region of interest. The average value of fluorescence intensity per pixel in the region of interest was then calculated using the digital image in the PE channel, as shown in FIG. 16. Using the spatial information of the image made it possible to eliminate a washing step and simplify the assay to a one-step homogeneous assay. FIG. 17 shows the calibration curve calculated in this example. Although a standard epi-fluorescence microscope was used in this example, a confocal or TIRF (total internal reflection fluorescence) microscope is preferred, because this type of microscope has better z-plane resolution, which can eliminate signals from above the focal plane where the microparticles are positioned, thereby lowering the background signal. A dilution step (adding buffer directly to the reaction mixture) right before the measurement can further reduce the fluorescence background from the excessive antibody conjugates, and thus improve the sensitivity of assays.

Another approach for eliminating the wash step in the immunoassay involves analysis by image correlation spectroscopy (ICS). Spatio-temporal image correlation spectroscopy (STICS) analysis is an extension of ICS where a series of images of the sample are acquired. These images include both spatial and temporal information; the conjugates bound to the microparticles via formation of a sandwich complex are immobile while the excess unbound conjugates are freely diffusing in the solution. STICS analysis can separate the immobile conjugate population from the diffusing conjugate population. There are other extensions of ICS, such as k-space Image Correlation Spectroscopy (kICS), and cross-correlation versions of ICS (CCICS) as well. Furthermore, by performing image correlation spectroscopy (ICS) analysis on the images, additional information about the sample can be acquired. For example, in diagnosing Alzheimer's disease, it is possible to use ICS to quantify the size of the amyloid plaques in an image as well as remove molecules undergoing diffusion.

Example 4

Figure 18:
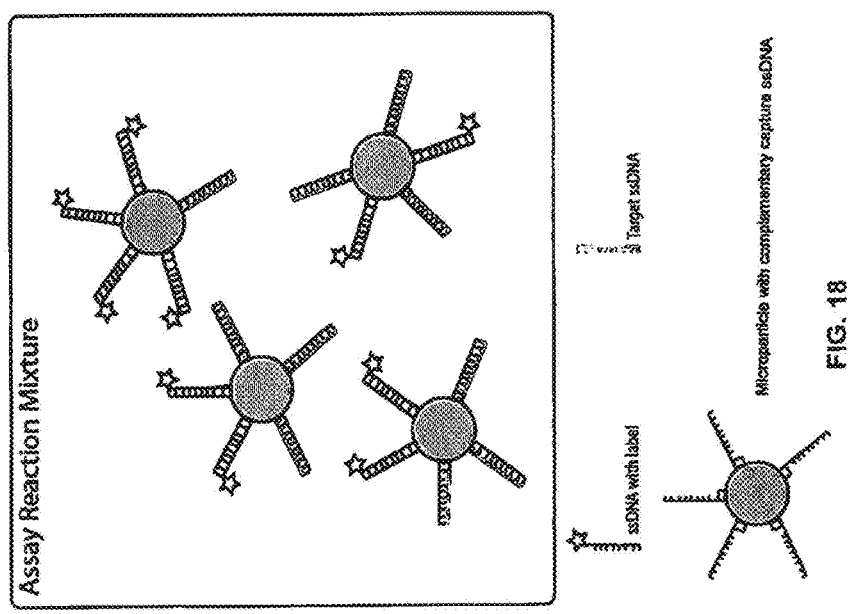
FIG. 18 is an illustration showing the protocol of an assay for detecting DNA.

This example illustrates how the method described herein can be used to detect DNA. In this case, the analyte is a target sequence of DNA and the receptor is the DNA strand complementary to the target sequence. For detection, a labeled DNA strand having a sequence identical to the target sequence is used. The principle of a competitive assay for a DNA target is shown in FIG. 18.

In this example, single-stranded DNA (ssDNA) immobilized on microparticles is mixed with a sample suspected of containing target ssDNA and incubated. The mixture also contains ssDNA identical to the target ssDNA but having a fluorescent label for determining the concentration of DNA. The ssDNA that is attached to a fluorescent label will be blocked by the presence of the target ssDNA. Therefore, if no fluorescence is detected, it can be concluded that the sample contains a sufficient amount of ssDNA to completely block the ssDNA having the fluorescent label. This condition would indicate a positive result. On the other hand, if there are no target ssDNA molecules in the sample, the ssDNA immobilized on the microparticles will be completely labeled with ssDNA having a fluorescent label. The reaction mixture shown in FIG. 18 illustrates the case in which the sample does contain target ssDNA, but not enough to completely block binding of the ssDNA having the fluorescent label. Therefore, both target ssDNA and ssDNA having a fluorescent label will be present and the fluorescence intensity will correspond inversely with the amount of target ssDNA in the sample.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the concentration of an analyte in a sample comprising the steps of:
   (a) combining in a reaction mixture (i) a sample suspected of containing an analyte, (ii) a first receptor attached to a microparticle that binds to the analyte, and (iii) a fluorescently labeled second receptor that binds to the analyte, and allowing formation of a complex comprising the microparticle attached to the first receptor, the analyte, and the fluorescently labeled second receptor;
   (b) acquiring a white light image of the reaction mixture in order to determine the location of the microparticle in the reaction of step (a) and a fluorescence image of the reaction mixture in order to determine the location of the fluorescently labeled second receptor in the reaction of step (a);
   (c) selecting at least one region of interest from the images acquired in step
   (b), wherein the at least one region of interest is a region from which light signals emanate from the complex formed in step (a);
   (d) selecting pixels in the at least one region of interest for analysis;
   (e) calculating and recording the average and variance of the counts per pixel for the pixels selected in step (d), wherein the counts per pixel is the number of photons counted per pixel per unit of time;
   (f) omitting pixels that have counts greater or less than a specified variance;
   (g) calculating average counts per pixel of the remaining pixels; and
   (h) determining the concentration of the analyte from the data in step (g).

2. The method of claim 1, wherein the images acquired in step (b) are digital images.

3. The method of claim 1, wherein only up to about two hundred (200) coated microparticles are required.

4. The method of claim 1, wherein the images acquired in step (b) are recorded by a fluorescence microscope equipped with a digital camera.

5. The method of claim 1, wherein a record of the assay is stored in computer data storage.

6. The method of claim 1, wherein the images acquired in step (b) are acquired and stored off-line.

7. The method of claim 1, wherein spatial information is used to qualify and quantify the results of a ligand-receptor binding assay.

8. The method of claim 1, wherein the analyte is an antigen, the first receptor is a capture antibody, and the second receptor is a detection antibody.

9. The method of claim 1, wherein the analyte is a target nucleic acid sequence, the first receptor is a capture nucleic acid sequence, and the second receptor is a fluorescently labeled nucleic acid sequence that is identical to the target nucleic acid sequence.

10. The method of claim 9, wherein the capture nucleic acid sequence is complementary to the target nucleic acid sequence.

11. The method of claim 9, wherein the target nucleic acid sequence is a DNA sequence or an RNA sequence.

12. The method of claim 9, wherein each of the target nucleic acid sequence, the capture nucleic acid sequence, and the fluorescently-labeled nucleic acid sequence is single stranded.

13. The method of claim 1, wherein the omitted pixels of step (f) have counts greater or less than two times the variance.

* * * * *